United States Patent

Carey et al.

[11] 4,333,877
[45] Jun. 8, 1982

[54] SUBSTITUTED 2,7-DIOXO-2,7-DIHYDROBENZO[1:2-B; 5:6-B¹]DIFURAN OR -DIPYRROLE DYESTUFFS, THEIR PREPARATION AND THEIR USE

[75] Inventors: John L. Carey, Rochdale; Colin W. Greenhalgh, Manchester, both of England

[73] Assignee: Imperial Chemical Industries Limited, London, England

[21] Appl. No.: 168,446

[22] Filed: Jul. 10, 1980

[30] Foreign Application Priority Data

Jul. 18, 1979 [GB] United Kingdom ................ 7925030

[51] Int. Cl.³ ................. C07D 209/56; C07D 307/77; C07D 493/04
[52] U.S. Cl. ........................................ 548/421; 8/471; 8/636; 8/922; 8/927; 260/340.5 R; 260/343.3 R; 548/429; 548/431; 549/435; 549/457; 549/458
[58] Field of Search ............... 260/325 R, 343.3 R, 260/340.5 R

[56] References Cited

U.S. PATENT DOCUMENTS 4,115,404  9/1978  Greenhalgh et al. ........... 260/325 R
4,122,087 10/1978  Greenhalgh et al. ........... 260/325 R Primary Examiner—Alton D. Rollins
Attorney, Agent, or Firm—Cushman, Darby & Cushman

[57] ABSTRACT

Dyestuffs having the general formula:

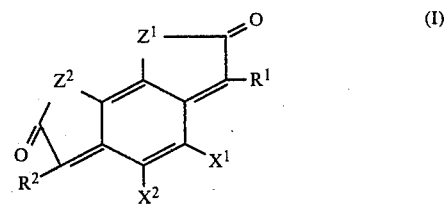

wherein
$Z^1$ and $Z^2$ each independently represent oxygen or $$-\underset{|}{N}Y$$

in which Y is hydrogen, an optionally substituted hydrocarbon radical or an acyl radical,
$R^1$ and $R^2$ each independently represent a substituted or unsubstituted aryl radical, preferably phenyl, and
$X^1$ and $X^2$ each independently represent hydrogen, halogen, cyano, alkyl, alkoxy, nitro, amino, substituted amino, carboxylic acid, carboxylic acid ester, optionally substituted carbamoyl, alkylthio, arylthio, alkylsulphonyl, arylsulphonyl, acyl, acyloxy, hydroxy, sulphonic acid or sulphonic acid ester, or
$X^1$ and $X^2$ together form a 5- or 6-membered, carbocyclic or heterocyclic, saturated or unsaturated, including aromatic, ring which may carry further substituents; processes for the manufacture of these dyestuffs and their use for coloring aromatic polyester textile materials.

4 Claims, No Drawings

SUBSTITUTED 2,7-DIOXO-2,7-DIHYDROBENZO[1:2-B; 5:6-B¹]DIFURAN OR -DIPYRROLE DYESTUFFS, THEIR PREPARATION AND THEIR USE

This invention relates to substituted 2,7-dioxo-2,7-dihydrobenzo[1:2-b; 5:6-b¹]difuran or -dipyrrole dyestuffs, their preparation and their use.

According to the present invention there are provided dyestuffs having the general formula:

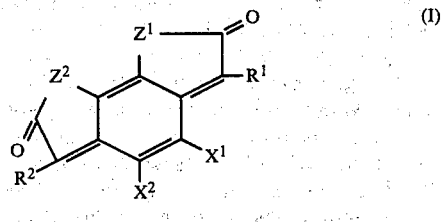

wherein
$Z^1$ and $Z^2$ each independently represent oxygen or

in which Y is hydrogen, an optionally substituted hydrocarbon radical or an acyl radical, $R^1$ and $R^2$ each independently represent an unsubstituted aryl radical or an aryl radical substituted by at least one of the following: nitro, halogen, alkyl, alkoxy, phenyl, alkoxyphenyl, phenoxy, cyano, carboxylic acid, carboxylic acid ester, optionally substituted carbamoyl, sulphonic acid, sulphonyl chloride, sulphonic acid ester, optionally substituted sulphamoyl, mercapto, alkylthio, arylthio, primary, secondary, tertiary or quaternary amino, acylamino, acyl, phosphonic acid, phosphonic acid ester, alkylsulphonyl, arylsulphonyl, aldehyde, acyloxy and hydroxy;

$X^1$ and $X^2$ each independently represent hydrogen, halogen, cyano, alkyl, alkoxy, nitro, amino, substituted amino, carboxylic acid, carboxylic acid ester, optionally substituted carbamoyl, alkylthio, arylthio, alkylsulphonyl, arylsulphonyl, acyl, acyloxy, hydroxy, sulphonic acid or sulphonic acid ester or $X^1$ and $X^2$ together form a 5- or 6-membered, carbocyclic or heterocyclic, saturated or unsaturated, including aromatic, ring which may carry further substituents.

The aryl radicals represented by $R^1$ and $R^2$ may be, for example, naphthyl radicals, but it is preferred that they are substituted or unsubstituted phenyl radicals.

It is further preferred that the alkyl and alkoxy radicals represented by $X^1$ and $X^2$ and which may be present as substituents on $R^1$ and $R^2$ are lower alkyl and lower alkoxy radicals respectively; also that the alkyl substituents of the alkylthio and alkylsulphonyl groups represented by $X^1$ and $X^2$ and which may be present as substituents on $R^1$ and $R^2$ are lower alkyl, that the aryl substituents of the arylthio and arylsulphonyl groups represented by $X^1$ and $X^2$ and which may be present as substituents on $R^1$ and $R^2$ are phenyl, and that the alkoxy substituent of the alkoxyphenyl groups which may be present as substituents on $R^1$ and $R^2$ is lower alkoxy.

The optionally substituted carbamoyl groups represented by $R^1$, $R^2$, $X^1$ and $X^2$ are preferably of the formula:

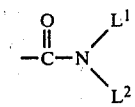

wherein $L^1$ and $L^2$ are each independently hydrogen, lower alkyl or phenyl. The carboxylic acid ester groups represented by $X^1$ and $X^2$ and which may be present as substituents on $R^1$ and $R^2$ are preferably of the formula —COOL³ wherein $L^3$ is an optionally substituted alkyl, in particular lower alkyl, or monocyclic aryl, in particular phenyl, radical.

The optionally substituted sulphamoyl groups which may be present as substituents on $R^1$ and $R^2$ are preferably of the formula:

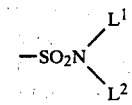

wherein $L^1$ and $L^2$ have the meanings defined above.

Examples of the optionally substituted hydrocarbon radicals represented by Y are alkyl and preferably lower alkyl such as methyl, ethyl, n-propyl and isopropyl, substituted alkyl and preferably substituted lower alkyl such as β-hydroxyethyl, β-methoxyethyl and β-ethoxyethyl, phenyl and substituted phenyl such as tolyl, chlorophenyl, nitrophenyl and lower alkoxyphenyl.

Examples of the acyl radicals represented by Y are acetyl, chloracetyl, phenylacetyl, propionyl, butyryl, isobutyryl, methylsulphonyl, p-toluenesulphonyl, unsubstituted benzoyl and benzoyl substituted by halogen, nitro, lower alkyl, lower alkoxy or hydroxy.

Examples of acylamino groups which may be present as substituents on $R^1$ and $R^2$ are acetylamino, propionylamino, benzoylamino, methanesulphonylamino, benzenesulphonylamino and toluenesulphonylamino.

Throughout this specification the terms "lower alkyl" and "lower alkoxy" are used to denote alkyl and alkoxy groups respectively containing from 1 to 4 carbon atoms.

The dyestuffs of the invention may be obtained by a number of methods, for example:

(a) Reaction of a compound of the formula:

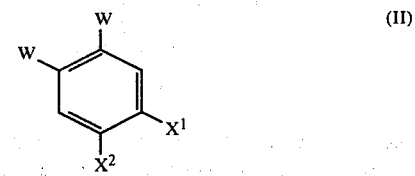

wherein $X^1$ and $X^2$ have the previously defined meanings and each W is —OH or —NHQ, or one W is —OH and the other is —NHQ, in which Q is hydrogen, optionally substituted alkyl, in particular lower alkyl, or optionally substituted monocyclic aryl, particularly phenyl, with an optionally substituted arylacetic acid or derived ester, an α-halogeno- or α-hydroxy optionally substituted arylacetic acid or derived ester or an O-acylated α-hydroxy optionally substituted arylacetic acid or derived ester.

The aryl radical of the arylacetic acid or derived ester may carry substituents, for example, nitro, lower alkyl, lower alkoxy, acylamino or halogen.

The conversion of a compound of formula (II) into the dyestuff of formula (I) by the above process involves an oxidation step. In some cases this takes place automatically in the presence of air, whilst in other cases it is preferred to treat the initial reaction product with an oxidising agent, such as nitrobenzene or an aqueous solution of hydrogen peroxide or potassium persulphate.

The reaction can be conveniently carried out by heating the two reactants together at elevated temperatures, optionally in the presence of an inert organic liquid (such as a di- or tri-chlorobenzene), or in the presence of an acid (such as acetic acid, sulphuric acid or polyphosphoric acid) or in the presence of an acidic agent such as zinc chloride. If desired an inert organic liquid can be used in conjunction with an acidic agent. The resulting product is then isolated in conventional manner; for example by filtering it off when it is insoluble in the reaction medium, or by adding a liquid to precipitate it from solution in the reaction medium and then filtering off the solid.

When it is preferred to include a deliberate oxidation treatment then this can be conveniently carried out by, for example, isolating the initial reaction product and subjecting this to oxidation, for example in a mixture of acetic acid and an aqueous solution of hydrogen peroxide or nitric acid. Alternatively the oxidation can be carried out without isolation of the initial reaction product by adding an oxidising agent, for example, nitrobenzene, to the reaction medium.

Examples of the compounds of formula (II) which may be used are catechol, 4-methylcatechol and 2,3-dihydroxynaphthalene.

Examples of the said arylacetic acids or esters thereof which may be used in the process are α-hydroxyphenylacetic acid (mandelic acid), phenylacetic acid, α-hydroxy-4-methoxyphenylacetic acid, methyl phenylacetate, α-chlorophenylacetic acid, 4-nitrophenylacetic acid, 4-acetylaminophenylacetic acid and 4-methoxyphenylacetic acid.

(b) Reaction of a compound of the formula:

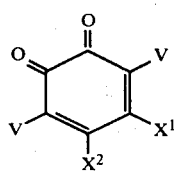

(III)

wherein $X^1$ and $X^2$ have the previously defined meanings and each V independently represents chlorine or bromine, with an optionally substituted arylacetic acid or derived ester, or an α-hydroxy optionally substituted arylacetic acid or derived ester as hereinbefore described.

The reaction may be carried out under the conditions described for process (a). No oxidation step is involved.

An example of the compound of formula (III) which may be used in process (b) in 3,4,5,6-tetrachloro-1,2-benzoquinone.

Dyestuffs in which either or both of $Z^1$ and $Z^2$ represent

may, if desired, be further reacted with an acylating agent to give the corresponding N-acyl derivatives, a reaction which is conveniently carried out in the presence of an acid-binding agent, for example, pyridine.

Examples of suitable acylating agents are carboxylic acid anhydrides such as acetic anhydride, n-propionic anhydride and n-butyric anhydride, and carboxylic acid halides such as isobutyryl chloride, benzoyl chloride, p-toluenesulphonyl chloride, methylsulphonyl chloride, phenylacetyl chloride and chloroacetyl chloride.

Having prepared dyestuffs by the said methods of synthesis other substituents can be introduced by conventional methods, or substituents already present can be converted to other substituents in known manner. The following are illustrative of such reactions:

(a) sulphonic acid groups can be introduced by sulphonation methods, and sulphonyl chloride groups by reaction with chlorosulphonic acid;

(b) nitro groups can be introduced by nitration methods;

(c) hydroxy groups can be converted to acyloxy groups by treatment with acylating agents;

(d) nitro groups can be reduced to amino groups;

(e) amino groups can be converted to acylamino groups by treatment with acylating agents, or into alkylamino groups by treatment with alkylating agents;

(f) tertiary amino groups can be converted to quaternary amino groups.

If desired the said dyestuff sturcture can also be incorporated into other dyestuff systems. Thus, for example, dyestuffs containing both the said dyestuff structure and an azo system can be prepared by coupling a diazotised amine on to a dyestuff of the present invention which contains a phenolic hydroxy group. Alternatively a dyestuff of the present invention which contains a diazotisable amino group can be diazotised and coupled on to a coupling component. Also a dyestuff of the present invention which additionally contains an azo group can be obtained by synthesis of the dyestuff structure directly from an intermediate which already contains an azo group. As a further example dyestuffs containing both the said dyestuff structure and a nitro dyestuff system can be obtained by, for example, condensing a dyestuff of the present invention containing an aminophenyl residue with a halogenonitrobenzene.

The dyestuffs of the invention are valuable for colouring natural and synthetic textile materials. Thus the dyestuffs of the invention which are free from water-solubilising groups (i.e. sulphonic acid, carboxylic acid or quaternary ammonium groups) are valuable for colouring synthetic textile materials, for example cellulose acetate and cellulose triacetate textile materials, polyamide textile materials such as polyhexamethylenedipamide textile materials, polyacrylonitrile textile materials and preferably aromatic polyester textile materials such as polyethylene terephthalate textile materials. Such textile materials can be in the form of threads, yarn, or woven or knitted fabric. If desired the textile material may be made from blends of natural and synthetic fibres. Examples of such materials are polyester/cellulose and polyester/wool textile materials.

Such textile materials can conveniently be coloured with the water-insoluble dyestuffs, as hereinbefore defined, by immersing the textile material in a dyebath comprising an aqueous dispersion of one or more of the said dyestuffs, which dyebath preferably contains a non-ionic, cationic and/or anionic surface-active agent, and thereafter heating the dyebath for a period at a suitable temperature. In the case of secondary cellulose acetate textile materials it is preferred to carry out the dyeing process at a temperature between 60° and 85° C.; in the case of cellulose triacetate or polyamide textile materials it is preferred to carry out the dyeing process at 95° to 100° C., in the case of aromatic polyester textile materials the dyeing process can either be carried out at a temperature between 90° and 100° C., preferably in the presence of a carrier such as diphenyl or o-hydroxydiphenyl, or at a temperature above 100° C., preferably at a temperature between 120° and 140° C., under superatmospheric pressure.

Alternatively, the aqueous dispersion of the said dyestuff can be applied to the textile material by a padding or printing process, followed by heating at temperatures up to 230° C. depending on the textile material, or by steaming of the textile material. In such processes it is preferred to incorporate a thickening agent, such as gum tragacanth, gum arabic or sodium alginate, into the aqueous dispersion of the said azo dyestuff.

At the conclusion of the colouring process it is preferred to give the coloured textile material a rinse in water or a brief soaping treatment before finally drying the coloured textile material. The dyestuffs of the present invention are also suitable for application to aromatic polyester or cellulose triacetate textile materials by the process described in United Kingdom Patent Specification No. 1,515,405, and to aromatic polyester/cellulose blends in conjunction with a reactive or other dyestuff for the cellulose component of the blend by the process described in United Kingdom Patent Specification No. 1,456,586, the dyestuff of the present invention taking the place of the dyestuff containing at least two carboxylic acid ester groups which is used in these processes. In these application methods the coloured textile material is subjected to a treatment in an aqueous solution of an alkali, such as sodium carbonate and especially sodium hydroxide, before the soaping treatment in order to remove loosely attached dyestuff from the surface of the textile material. The dyestuffs of the present invention can be used in the processes described in United Kingdom Patent Specification Nos. 1,515,405 and 1,456,586 by virtue of their containing lactone (and/or lactam) rings which are opened by the treatment with alkali, giving water-soluble derivatives which readily wash off the textile material.

The water-insoluble dyestuffs have excellent affinity and building up properties on aromatic polyester textile materials, so enabling deep shades to be obtained. The resulting colourations have good to excellent fastness to light, to wet treatments, to perspiration, and in particular to dry heat such as those carried out at high temperatures during pleating operations.

If desired the water-insoluble dyestuffs of the invention can be applied to synthetic textile materials in conjunction with other disperse dyes, such as are described in, for example, British Specifications, Nos. 806,271; 835,819; 840,903; 847,175; 852,396; 852,493; 859,899; 865,328; 872,204; 894,012; 908,656; 909,843; 910,306; 913,856; 919,424; 944,513; 944,722; 953,887; 959,816; 960,235; 961,412; 976,218; 993,162 and 998,858.

Those dyestuffs of the invention which are soluble in water by virtue of the presence of quaternary ammonium groups can be used as basic dyestuffs for the dyeing of polyacrylonitrile textile materials or of polyamide and polyester textile materials which contain acidic groups which confer affinity on such textile materials for basic dyestuffs. The said dyestuffs can be applied in conventional manner to these textile materials from acid, neutral or slightly alkaline dyebaths, the pH of which is preferably maintained in the range of 3 to 8, at temperatures between 40° C. and 120° C., preferably between 80° C. and 120° C., or by printing techniques using thickened print pastes containing the said dyestuffs.

Those dyestuffs of the invention which are soluble in water by virtue of the presence of acidic water-solubilising groups can be used for colouring natural or synthetic polyamide textile materials such as wool, silk or polyhexamethylene adipamide textile materials. Such dyestuffs can be applied in conventional manner to the said textile materials from aqueous dyebaths, the pH of which is preferably maintained in the range of 4 to 9.

Those dyestuffs of the invention which contain acidic water-solubilising groups can be used for colouring cellulose textile materials, the dyestuffs being applied by conventional methods to such textile materials. Dyestuffs of the invention which contain fibre-reactive groups in addition to acidic water-solubilising groups are also suitable for application to cellulosic textile materials.

Dyestuffs of the invention can also be applied to textile materials by transfer printing processes, including such processes carried out at reduced pressures or under moist or humid conditions. Dyestuffs of the invention can also be used in mass colouration processes.

Insoluble dyestuffs of the present invention can also be used as pigments for the colouration of inks and paints, such dyestuffs being incorporated in known manner into conventional ink or paint formulations.

The invention is illustrated by the following Examples in which the parts and percentages are by weight.

EXAMPLE 1

A mixture of 6.6 parts of catechol and 18.3 parts of mandelic acid is heated at 195°–200° C. for 5 hours when 6 parts of nitrobenzene are added. The mixture is stirred and heated at 195°–200° C. for a further 0.75 hour. The reaction mixture is then cooled, 25 parts of toluene are added, the mixture is heated to the boil and then allowed to cool to 20° C. The precipitated product is filtered off and recrystallised from toluene to give 3,6-diphenyl-2,7-dioxo-2,7-dihydrobenzo[1:2-b; 5:6-b¹]difuran as orange crystals, m.p. 259°–260° C. The mass spectrum of the compound shows an intense molecular ion at 340 consistent with this structure. The dyestuff dissolves in toluene to give an orange solution with λ max 474 n.m. and molecular extinction coefficient of 49,700.

When dispersed in aqueous medium this dyestuff dyes aromatic polyester materials in bright orange shades having excellent fastness to light. Any unfixed dyestuff on the surface of the fibre is readily removed by treatment with a dilute aqueous solution of sodium hydroxide at 80° C.

EXAMPLE 2

A mixture of 1.24 parts of 4-methyl catechol and 5.46 parts of 4-methoxymandelic acid is stirred and heated at 180°–190° C. for 3 hours. 2 Parts of nitrobenzene are added and this mixture is stirred at 180°–190° C. for a further 3 hours. After cooling to 40° C. the reaction mixture is diluted with 25 parts of methanol and allowed to cool to 20° C. The precipitated 4-methyl-3,6-di-(4-methoxyphenyl)-2,7-dioxo-2,7-dihydrobenzo[1:2-b; 5:6-b¹]difuran is filtered off, washed with methanol and dried. The product has m.p. 216°–217° C. and the mass spectrum shows a strong molecular ion at 414 consistent with this structure. The dyestuff dissolves in chloroform to give a red solution with λ max 504 and extinction coefficient of 30,200. When dispersed in aqueous medium this dyestuff dyes aromatic polyester materials in bright scarlet shades showing good build up properties and good fastness to light.

EXAMPLE 3

A mixture of 2.5 parts of 4-methylcatechol and 9.1 parts of mandelic acid is stirred and heated at 190°–200° C. for 18 hours. After cooling, the reaction mixture is diluted with 25 parts of methanol, and the precipitated product is filtered off and recrystallised by methanol extraction. The 4-methyl-3,6-diphenyl-2,7-dioxo-2,7-dihydrobenzo[1:2-b; 5,6-b¹]difuran so obtained has m.p. 229°–231° C. and the mass spectrum shows a strong molecular ion at 354. The dyestuff dissolves in chloroform to give a yellow solution with λmax 444 n.m. and a molecular extinction coefficient of 42,100.

When dispersed in aqueous medium the dyestuff dyes aromatic polyester materials in reddish-yellow shades showing good build up properties and excellent fastness to light.

EXAMPLE 4

A mixture of 2.46 parts of 3,4,5,6-tetrachloro-1,2-benzoquinone, 4.98 parts of 4-methoxyphenylacetic acid and 8 parts of trichlorobenzene is stirred and heated at 185°–195° C. for 4 hours. After cooling to 40° C. the reaction mixture is diluted with 25 parts of ethanol, cooled to 20° C. and the product is filtered off, washed with ethanol and dried. Recrystallisation from toluene gives 4,5-dichloro-3,6-di(4-methoxyphenyl)-2,7-dioxo-2,7-dihydrobenzo[1:2-b; 5:6-b¹]difuran with m.p. 266°–267° C. The mass spectrum gives a strong molecular ion at 468 consistent with this structure. In toluene the product gives a red solution with λ max 540 n.m. and molecular extinction coefficient 45,000.

When applied to aromatic polyester materials from aqueous dispersion the dyestuff gives bright bluish-red shades with good build up properties and good fastness to light.

EXAMPLE 5

A mixture of 2.46 parts of tetrachloro-1,2-benzoquinone, 4.1 parts of phenylacetic acid and 8 parts of trichlorobenzene is stirred and heated at 185°–190° C. for 3 hours. After cooling, 40 parts of ethanol are added followed by petroleum ether (b.p. 80°–100° C.) to precipitate the crude produce as an oil. Purification by chromatography on a silica gel column using toluene containing 5% acetone as eluent gives 4,5-dichloro-3,6-diphenyl-2,7-dioxo-2,7-dihydrobenzo[1:2-b; 5:6-b¹]difuran having m.p. >350° C. In chloroform solution the product gives an orange solution with λ max 447 n.m. and molecular extinction coefficient of 29,500. The mass spectrum terminates in a molecular ion at 408 indicating the presence of two chlorine³⁵ atoms fully consistent with the proposed structure.

When applied to aromatic polyester material from an aqueous dispersion the product gives orange shades with good fastness to light.

EXAMPLE 6

A mixture of 32 parts of 2,3-dihydroxynaphthalene and 92 parts of mandelic acid is stirred and heated at 200°–205° C. in a gentle stream of air for 3 hours whilst allowing the formed water to distil off. 20 Parts of nitrobenzene are then added and heating is continued until no more water is evolved (approximately 0.5 hour). The reaction mixture is then cooled to approximately 90° C. when 100 parts of toluene are added and the mixture is allowed to cool to 20° C. The precipitated product is filtered off and may be recrystallised from toluene. The 3,8-diphenyl-2,9-dioxo-2,9-dihydronaphtho[2:1-b; 3:4-b¹]difuran is obtained as yellow crystals having m.p. 262°–266° C. The mass spectrum shows a strong molecular ion at 390 consistent with this structure. When dissolved in chloroform the product gives a yellow solution with λ max 420 n.m. and molecular extinction coefficient 37,000.

When applied to aromatic polyester textile materials from aqueous dispersion the product gives bright greenish-yellow shades with good build up properties and excellent fastness to light.

EXAMPLE 7

A mixture of 1.68 parts of 2,3-dihydroxynaphthalene and 3.64 parts of 4-methoxymandelic acid is stirred and heated at 185°–190° C. for 30 minutes, by which time the melt has almost solidified. 2 Parts of nitrobenzene are then added and heating is continued for 1.5 hours. After cooling to 100° C., 25 parts of toluene are added. The reaction mixture is allowed to cool to 20° C. and the precipitated product is filtered off, washed with methanol and dried. The 3,8-di(4-methoxyphenyl)-2,9-dioxo-2,9-dihydronaphtho[2:1-b; 3:4-b¹]difuran obtained melts at 303°–304° C. The mass spectrum shows a strong molecular ion at 450 consistent with this structure.

When dissolved in chloroform the product gives an orange solution with λ max 465 n.m. and molecular extinction coefficient 34,400.

When applied to aromatic polyester textile materials from an aqueous dispersion the product gives bright orange shades with good fastness to light.

EXAMPLE 8

A mixture of 1.68 parts of 4,5-dimethoxy-1,2-benzoquinone and 5 parts of phenylacetic acid is stirred and heated at 170° C. for 2 hours, then cooled to 50° C. 10 Parts of ethanol are added. After cooling the reaction mixture to 20° C. and allowing it to stand for several hours the precipitated 3,7-di(4-methoxyphenyl)-4,5-dimethoxy-2,7-dioxo-2,7-dihydrobenzo[1:2-b; 5,6-b¹]difuran is filtered off, washed with ethanol and dried. The product has m.p. 210°–212° C. and the mass spectrum shows a strong molecular ion at 460 consistent with this structure. When dissolved in chloroform the product gives a red solution with λ max 512 n.m. and molecular extinction coefficient 43,000.

When applied to aromatic polyester textile materials from aqueous dispersion the product gives bright red shades with good fastness to light.

EXAMPLE 9

A mixture of 1.1 parts of catechol and 5.46 parts of 4-methoxymandelic acid is heated at 190°–195° C. for 3 hours, when 2 parts of nitrobenzene are added. After a further 0.5 hour at 190°–195° C. the reaction mixture is cooled, diluted with methanol and the product isolated by filtration to give 3,6-di-(4-methoxyphenyl)-2,7-dioxo-2,7-dihydrobenzo-[1:2-b; 5:6-b¹]difuran, m.p. 250° C. (indistinct). The mass spectrum gives a strong molecular ion at 400 consistent with this structure. The product dissolves in chloroform to give a red solution. λ max 534 nm, ε max 32,000. The product dyes aromatic polyester material from an aqueous dispersion in bright bluish red shades. This product is also obtained when the reaction is carried out in 1,2-dichlorobenzene followed by oxidation with nitrobenzene, reaction conditions being similar to those described in Example 12.

EXAMPLE 10

A mixture of 2.5 parts of 1,2,4-trihydroxybenzene, and 9.1 parts of mandelic acid is heated at 190°–200° C. for 18 hours when 2 parts of nitrobenzene are added and heating is continued for 1 hour. After cooling, the reaction mixture is diluted with toluene, the product isolated by filtration and impurities removed by extraction with toluene to give 4-hydroxy-3,6-diphenyl-2,7-dioxo-2,7-dihydrobenzo[1:2-b; 5:6-b¹]difuran having m.p. 352° C. The mass spectrum gives a molecular ion at 356 consistent with this structure and the product dissolves in acetone/methanol (9:1) to give an orange solution having λ max 455 nm, ε max 36,100. The product dyes polyester in orange-brown shades.

EXAMPLE 11

In place of the mandelic acid used in Example 6 there is used an equivalent amount of 4-methylmandelic acid. The 3,8-di(4-tolyl)-2,9-dioxo-2,9-dihydronaphtho-[2:1-b; 3:4-b¹]difuran so obtained has m.p. 280°–281° C., and the mass spectrum has a molecular ion at 418 consistent with this structure. The dyestuff dissolves in chloroform to give a yellow solution having λ max 438 nm, ε max 41,700. When applied to aromatic polyester textile materials from aqueous dispersion either by a batchwise dyeing process or by a printing process involving fixation at 180° C. or by a transfer printing technique, bright yellow shades are produced with good fastness properties.

When admixed in a ratio of 1:1 with the dyestuff of Example 6 yellow shades are obtained on polyester which show improved build up properties over the single components.

EXAMPLE 12

A mixture of 1.6 parts of 2,3-dihydroxynaphthalene, 5.0 parts of 3-methylmandelic acid and 25 parts of 1,2-dichlorobenzene is heated under reflux for 20 hours when 2.5 parts of nitrobenzene are added and heating continued for a further 3 hours. After cooling, the product is isolated by filtration to give 3,8-di(3-tolyl)-2,9-dioxo-2,9-dihydronaphtho[2:1-b; 3:4-b¹]difuran having m.p. 246° C. The mass spectrum shows a molecular ion at 418 consistent with this structure. The dyestuff dissolves in chloroform to give a yellow solution having λ max 424, ε max 36,000. The product dyes polyester in bright yellow shades having good fastness properties.

When admixed in a ratio of 1:1 with the dyestuffs of Example 6, Example 11 or Example 13 yellow shades are obtained on polyester which show improved build up properties over the single components.

EXAMPLE 13

3,8-Di(3-chlorophenyl)-2,9-dioxo-2,9-dihydronaphtho-[2:1-b; 3:4-b¹]difuran may be obtained by the method of Example 12 using 3-chloromandelic acid in place of the 3-methylmandelic acid, the product being precipitated from the cooled reaction mixture by the addition of a 4:1 mixture of petroleum ether (b.p. 40°–60°) and ethanol. The dyestuff has m.p. 248° C. and dissolves in chloroform to give a yellow solution having λ max 414 nm, ε max 33,200. When applied to polyester from aqueous dispersions the dyestuff gives bright yellow shades having good fastness properties.

EXAMPLE 14

3,8-Di(2-chlorophenyl)-2,9-dioxo-2,9-dihydronaphtho-[2:1-b; 3:4-b¹]difuran may be obtained by the method of Example 7 using 2-chloromandelic acid in place of the 4-methoxymandelic acid and a reaction time of 3 hours before adding the nitrobenzene. The dyestuff has m.p. 266° C. and gives a yellow solution in chloroform having λ max 395, ε max 36,000. The dyestuff gives greenish-yellow shades on polyester with moderate build up properties. When admixed in a 1:1 ratio with the dyestuff of Example 15 bright yellow shades are obtained on polyester which show better build up properties than either component.

EXAMPLE 15

3,8-Di(4-chlorophenyl)-2,9-dioxo-2,9-dihydronaphtho-[2:1-b; 3:4-b¹]difuran may be obtained by the method of Example 7 using 4-chloromandelic acid in place of the 4-methoxymandelic acid and a reaction time of 2 hours before adding the nitrobenzene. The dyestuff has m.p. 312° C. and gives a yellow solution in chloroform having λ max 430 nm, εmax 34,800. The mass spectrum shows a molecular ion at 458 consistent with this structure. The dyestuff gives bright yellow shades on polyester showing good build up and fastness properties. When admixed in a ratio of 1:1 with the dyestuff of Example 6 yellow shades having excellent build up properties on polyester are obtained.

EXAMPLE 16

3,8-Di(3,4-methylenedioxyphenyl)-2,9-dioxo-2,9-dihydronaphtho[2:1-b; 3:4-b¹]difuran may be obtained by the method of Example 7 using methylenedioxymandelic acid in place of the 4-methoxymandelic acid, with a reaction time of 3 hours before adding the nitrobenzene. The dyestuff has m.p. 292° C. and gives a reddish-orange solution in chloroform having λmax 485 nm, εmax 25,800. The mass spectrum shows a molecular ion at 478 consistent with this structure. The dyestuff gives bright scarlet shades on polyester.

EXAMPLE 17

3,8-Dinaphthyl-2,9-dioxo-2,9-dihydronaphtho-[2:1-b; 3:4-b¹]difuran may be obtained by the method of Example 7 using α-naphthylglycolic acid in place of the 4-methoxymandelic acid, with a reaction time of 1 hour before adding the nitrobenzene. The mass spectrum gives a molecular ion at 490 consistent with this structure. The product dyes aromatic polyester material in yellow shades from an aqueous dispersion.

EXAMPLE 18

A mixture of 1.6 parts of 2,3-dihydroxynaphthalene, 1.55 parts of mandelic acid and 25 parts of 1,2-dichlorobenzene is heated under reflux for 2 hours. 3.3 Parts of 3-methylmandelic acid are then added and the mixture is heated under reflux for a further 18 hours. 2.5 Parts of nitrobenzene are added and heating continued for a further 3 hours. The reaction mixture is cooled and the precipitated product is filtered off, washed with petroleum ether (b.p. 60°–80° C.) and dried. The product consists of a mixture of 3,8-diphenyl-2,9-dioxo-2,9-dihydronaphtho-[2:1-b; 3:4-b¹]difuran, 3,8-di(3-tolyl)-2,9-dioxo-2,9-dihydronaphtho[2:1-b; 3:4-b¹]difuran and 3-phenyl-8-(3-tolyl)-2,9-dioxo-2,9-dihydronaphtho[2:1-b; 3:4-b¹]difuran and has m.p. 245° C. When applied to aromatic polyester textile materials from aqueous dispersion yellow shades are obtained which show improved build up properties over the dyestuffs of Examples 6, 12 and 20.

EXAMPLE 19

A mixture of 2.76 parts of 4-hydroxy-1-phenyl-2-oxo-1,2-dihydronaphtho[2:1-b]furan, 3.5 parts of 4-methoxy mandelic acid and 25 parts of 1,2-dichlorobenzene is heated under reflux for 20 hours when 3 parts nitrobenzene are added and heating is continued for a further 2 hours. After cooling, the product is isolated by filtration to give 3-phenyl-8-(4-methoxyphenyl)-2,9-dioxo-2,9-dihydronaphtho-[2:1-b; 3:4-b¹]difuran, m.p. 238° C. The product gives an orange solution in chloroform having λmax 447 nm, εmax 31,500. The product dyes aromatic polyester textile materials in bright orange shades with good build up and fastness properties.

The 4-hydroxy-1-phenyl-2-oxo-1,2-dihydronaphtho-[2:1-b]furan used in the above Example may itself be prepared as follows:

A solution of 25 parts of 2,3-dihydroxynaphthalene and 25 parts of mandelic acid in 100 parts of 1,2-dichlorobenzene is heated under reflux for 20 hours. The reaction mixture is cooled and the product is filtered off, washed with ethanol and dried. The intermediate has m.p. 231° C.

EXAMPLE 20

3-Phenyl-8-(3-tolyl)-2,9-dioxo-2,9-dihydronaphtho-[2:1-b; 3:4-b¹]difuran may be obtained by the method of Example 19 by replacing the 4-methoxymandelic acid by 3-methylmandelic acid. The dyestuff obtained has m.p. 257° C. and dissolves in chloroform to give a yellow solution having λmax 422.5 nm and εmax 33,300. The product dyes aromatic polyester material from aqueous dispersion in bright yellow shades with better build up than the dyestuffs obtained in Examples 6 and 12.

EXAMPLE 21

3-(4-tolyl)-8-(4-methoxyphenyl)-2,9-dioxo-2,9-dihydronaphtho[2:1-b; 3:4-b¹]difuran may be obtained in an analogous manner to the product of Example 19. The product has m.p. 272° C. and dissolves in chloroform to give an orange solution having λmax 453 nm, εmax 31,600. The product dyes aromatic polyester textile materials from an aqueous dispersion in bright orange shades.

EXAMPLE 22

3-Naphthyl-8-(4-tolyl)-2,9-dioxo-2,9-dihydronaphtho-[2:1-b; 3:4-b¹]difuran may be obtained in an analogous manner to the product of Example 19 by the reaction of 2,3-dihydroxynaphthalene with 1-naphthylamine to give 4-hydroxy-1-naphthyl-2-oxo-1,2-dihydronaphtho[2:1-b]furan which is then reacted with 4-methylmandelic acid. The product so obtained has m.p. 253° C. and dissolves in chloroform to give an orange solution, λmax 434 nm, εmax 23,000. The product dyes aromatic polyester textile materials in orange shades.

EXAMPLE 23

5,6-Dibromo-3,8-diphenyl-2,9-dioxo-2,9-dihydronaphtho[2:1-b; 3:4-b¹]difuran may be prepared by the method of Example 7 by reacting 1,4,5,6-tetrabromo-2,3-dihydroxynaphthalene with mandelic acid in the presence of nitrobenzene using a reaction time of 4 hours. The product gives a mass spectrum with a molecular ion at 548 consistent with this structure and the product dissolves in chloroform to give a yellow solution having λmax 429 nm and εmax 38,700. The product gives yellow shades on polyester textile materials.

EXAMPLE 24

A mixture of 4.76 parts of 1,4,6,7-tetrabromo-2,3-dihydroxynaphthalene, 4.98 parts of 4-methoxyphenylacetic acid and 8 parts of 1,2,4-trichlorobenzene is heated at 190°–195° C. for 4 hours. After cooling, the product is isolated by filtration to give 5,6-dibromo-3,8-di(4-methoxyphenyl)-2,9-dioxo-2,9-dihydronaphtho[2:1-b; 3:4-b¹]difuran. The mass spectrum gives a molecular ion at 606. The product dissolves in chloroform to give an orange solution having λmax 482 nm and εmax 31,000. The product gives orange shades when applied to aromatic polyester textile materials.

EXAMPLE 25

A mixture of 2.26 parts of 4-hydroxy-1-phenyl-2-oxo-1,2-dihydrobenzo[1:2-b]furan and 2.0 parts of 4-chloromandelic acid is heated at 185°–190° C. for 0.5 hour when 2 parts of nitrobenzene are added and heating is continued for a further 0.5 hour. After cooling, ethanol is added and the precipitated 3-phenyl-6-(4-chlorophenyl)-2,7-dioxo-2,7-dihydrobenzo[1:2-b; 5:6-b¹]difuran is filtered off, washed successively with ethanol and petroleum ether and dried. The dyestuff melts at 279° C. and the mass spectrum shows a molecular ion at 374 consistent with this structure. When dissolved in chloroform an orange solution is obtained having λmax 476 nm and molecular extinction coefficient of 47,800.

When dispersed in aqueous medium this dyestuff dyes aromatic polyester materials in bright orange shades showing good build up properties and good fastness properties.

The 4-hydroxy-1-phenyl-2-oxo-1,2-dihydrobenzo-[1:2-b]furan used in this Example may be obtained in the following manner:

A mixture of 10 parts of mandelic acid, 14 parts of catechol and 25 parts of 73% sulphuric acid is heated at 75°–80° C. for 1.5 hours, cooled to 20° C. and the slightly sticky product isolated by decantation. The crude intermediate is washed by decantation with 73% sulphuric acid and then with water when it solidifies and can be isolated by filtration and then dried. The intermediate can be further purified by recrystallisation from petroleum ether (b.p. 100°–120° C.) when it has m.p. 134°-135° C. The intermediate can also be made by a similar method to that described in Example 19 for the preparation of 4-hydroxy-1-phenyl-2-oxo-1,2-dihydronaphtho[2:1-b]furan.

EXAMPLE 26

3-Phenyl-8-(4-ethoxy-3-methoxyphenyl)-2,9-dioxo-2,9-dihydronaphtho[2:1-b; 3:4-b¹]difuran may be obtained by the method of Example 19 by replacing the 4-methoxymandelic acid with 4-ethoxy-3-methoxymandelic acid. The mass spectrum terminates in a molecular ion at 464 and a fragmentation pattern in full support of the structure. The product has m.p. 285° C. and dissolves in chloroform to give an orange solution having λmax 440. The product dyes aromatic polyester textile materials from an aqueous dispersion in orange shades.

EXAMPLE 27

A mixture of 1.6 parts of 3-amino-2-naphthol, 5.46 parts of 4-methoxymandelic acid and 25 parts of 1,2-dichlorobenzene is heated under reflux for 20 hours when 2.5 parts of nitrobenzene are added and heating is continued for a further 1½ hours. After cooling, the mixture is diluted with 50 parts of ethanol. The highly crystalline product is isolated by filtration to give 1,6-di(4-methoxyphenyl)-4,5-dihydro-2H-3-oxa-4-azabenz-[e]-as-indacene having m.p. 340° C. The dyestuff dissolves in chloroform to give an orange solution having λmax 464 nm, εmax 35,000. When applied to aromatic polyester textile materials from aqueous dispersion by batchwise dyeing orange shades are obtained.

EXAMPLE 28

A mixture of 0.5 parts of 5-nitro-2,3-dihydroxynaphthalene, 1.4 parts of 4-methoxymandelic acid and 10 parts of 1,2-dichlorobenzene is heated under reflux for 20 hours when 1 part of nitrobenzene is added and heating is continued for a further 1 hour. After cooling, the mixture was diluted with ethanol and the product isolated by filtration to give 3,8-di-(4-methoxyphenyl)-4-nitro-2,9-dioxo-2,9-dihydronaphtho[2:1-b; 3:4-b¹]difuran. The mass spectrum shows a molecular ion at 495 consistent with this structure. The dyestuff gives orange brown shades on polyester textile materials.

EXAMPLE 29

1,6-Diphenyl-4,5-dihydro-2H-3-oxa-4-azabenz-[e]-as-indacene may be prepared by the method of Example 27 replacing the 4-methoxymandelic acid with an equivalent amount of mandelic acid. The dyestuff dissolves in chloroform to give a yellow solution having λmax 414 nm and dyes aromatic polyester textile materials in yellow shades.

EXAMPLE 30

A mixture of 5.1 parts of 4-hydroxy-1-phenyl-2-oxo-1,2-dihydrobenzo[1:2-b]furan made as described in in Example 25, and 5 parts of 4-methoxymandelic acid may be reacted as in Example 7 or Example 19 to give 3-phenyl-6-(4-methoxyphenyl)-2,7-dioxo-B 2,7-dihydrobenzo[1:2-b; 5:6-b¹]-difuran having m.p. 254° C. The mass spectrum contains a molecular ion at 370 and the dyestuff dissolves in chloroform to give a red solution having λmax 508 nm and εmax 45,000. The product dyes aromatic polyester textile materials in bright red shades.

We claim:

1. Dyestuffs characterised by the general formula:

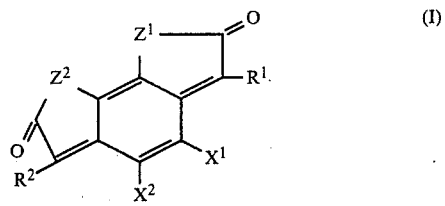

wherein $Z^1$ and $Z^2$ each independently represent oxygen or —NH—; $R^1$ and $R^2$ each independently represent unsubstituted naphthyl, unsubstituted phenyl, 3,4-methylenedioxyphenyl or phenyl substituted by at least one of $C_1$–$C_4$ alkyl, $C_1$–$C_4$ alkoxy, nitro, acetylamino, or halogen; $X^1$ and $X^2$ each independently represent hydrogen, $C_1$–$C_4$ alkyl, $C_1$–$C_4$ alkoxy, halogen or hydroxy, or $X^1$ and $X^2$ together form a 6-membered benzene ring which is unsubstituted or substituted by at least one of halogen or nitro.

2. Dyestuffs as claimed in claim 1 characterised in that $R^1$ and $R^2$ are unsubstituted phenyl.

3. A process for the manufacture of the dyestuffs claimed in claim 1 characterised in that a compound of the formula

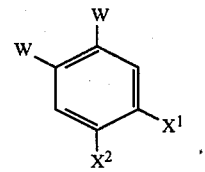

wherein $X^1$ and $X^2$ have the meanings stated in claim 1 and each W is —OH or —NH₂, or one W is —OH and the other is —NH₂ is reacted with an acetic acid derivative selected from the group consisting of naphthylacetic acid, alpha-hydroxynaphthylacetic acid, phenylacetic, alpha-halogenophenylacetic and alpha-hydroxyphenylacetic acids in which the phenyl nucleus is unsubstituted or which is substituted by at least one of $C_1$–$C_4$ alkyl, $C_1$–$C_4$ alkoxy, halogen, nitro or acetylamino, methylenedioxymandelic acid and $C_1$–$C_4$ alkyl esters of these acids followed by oxidation of the initial reaction product.

4. A process for the manufacture of the dyestuffs claimed in claim 1, characterised in that a compound of the formula:

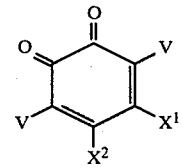

wherein $X^1$ and $X^2$ have the meanings stated in claim 1 and each V independently represents chlorine or bromine, is reacted with an acetic acid derivative selected from the group consisting of naphthylacetic acid, alpha-hydroxynaphthylacetic acid, phenylacetic and alpha-hydroxyphenylacetic acids in which the phenyl nucleus is unsubstituted or which is substituted by at least one of $C_1$–$C_4$ alkyl, $C_1$–$C_4$ alkoxy, halogen, nitro or acetylamino, methylenedioxymandelic acid and $C_1$–$C_4$ alkyl esters of these acids.

* * * * *